US010695076B2

(12) United States Patent
Agunloye et al.

(10) Patent No.: US 10,695,076 B2
(45) Date of Patent: Jun. 30, 2020

(54) GUIDED OSTEOTOME

(71) Applicant: DEPUY IRELAND UNLIMITED COMPANY, County Cork (IE)

(72) Inventors: Marcus Agunloye, Newport (GB); Alec Birkbeck, Leeds (GB); Graeme Dutton, Burnley (GB); David Horne, Leeds (GB); Thomas Maack, Batley (GB); John Bohannon Mason, Charlotte, NC (US); Richard Patnelli, Leeds (GB)

(73) Assignee: DEPUY IRELAND UNLIMITED COMPANY (IE)

( * ) Notice: Subject to any disclaimer, the term of this patent is extended or adjusted under 35 U.S.C. 154(b) by 565 days.

(21) Appl. No.: 15/472,534

(22) Filed: Mar. 29, 2017

(65) Prior Publication Data

US 2018/0280036 A1  Oct. 4, 2018

(51) Int. Cl.
*A61B 17/17* (2006.01)
*A61B 17/16* (2006.01)

(52) U.S. Cl.
CPC ...... *A61B 17/1735* (2013.01); *A61B 17/1659* (2013.01); *A61B 17/1668* (2013.01); *A61B 17/175* (2013.01)

(58) Field of Classification Search
CPC .............. A61B 17/164; A61B 17/1688
See application file for complete search history.

(56) References Cited

U.S. PATENT DOCUMENTS

| 5,041,118 | A | * | 8/1991 | Wasilewski | ........ A61B 17/1659 606/85 |
| 5,593,451 | A | | 1/1997 | Averill | |
| 5,665,090 | A | | 9/1997 | Rockwood | |
| 6,319,256 | B1 | | 11/2001 | Spotorno | |
| 8,529,569 | B2 | * | 9/2013 | Smith | ................ A61B 17/00 606/79 |
| 2002/0058999 | A1 | * | 5/2002 | Dwyer | ................ A61F 2/30734 623/22.42 |
| 2004/0138756 | A1 | | 7/2004 | Reeder | |
| 2011/0160733 | A1 | | 6/2011 | Wallstein | |
| 2015/0057666 | A1 | | 2/2015 | Kelley | |
| 2015/0119892 | A1 | | 4/2015 | Witt | |
| 2015/0119893 | A1 | | 4/2015 | Witt | |
| 2016/0095606 | A1 | | 4/2016 | Carver | |
| 2016/0262770 | A1 | | 9/2016 | Kelman | |

FOREIGN PATENT DOCUMENTS

WO  WO 1990003764 A1  4/1990
WO  WO 2016071516 A1  5/2016

* cited by examiner

*Primary Examiner* — Andrew Yang

(57) ABSTRACT

The invention provides an osteotome which includes a curved guide member extending distally from its medial side. This curved guide member interfaces with the medial curvature of the femoral canal. The guide member guides the osteotome using the internal bone geometry of the femoral canal instead of relying on external anatomical landmarks.

14 Claims, 4 Drawing Sheets

GUIDED OSTEOTOME

FIELD OF THE INVENTION

This invention relates to instruments and methods used for preparing a patient's femur prior to implantation of a femoral component of a hip prosthesis during hip arthroplasty.

BACKGROUND OF THE INVENTION

In total hip replacement surgery, a patient's natural hip is replaced by an acetabular cup component that replaces the acetabular socket and a femoral component that replaces the femoral head.

The femoral component of the hip prosthesis includes a generally spherical head, connected via a neck portion, to an elongate stem. The patient's femur is prepared to receive the stem. The proximal end of the femur is resected to expose the medullary canal. This involves resection of at least part of the greater femoral trochanter, and the creation of a cavity that matches the shape of the implant stem.

Surgeons may use several different instruments such as an osteotome, rasp, canal probe, and starter broach to initiate the canal. Changing between instruments takes time. Additionally, the number of instruments required for surgery indirectly increases cost of a procedure.

There is therefore a need for a multifunctional instrument that combines the functionality of existing instruments.

To help ensure proper final orientation of the stem, lateral bias during implant preparation may be preferred. Retraction of the gluteus medius and removal of the lateral cortical bone at the trochanteric fossa helps the surgeon to obtain optimal proximal fit of the stem. This also reduces the risk of undersizing and/or varus placement of the stem.

Surgeons currently face several challenges when using traditional osteotomes. For example, the surgeon conventionally positions the osteotome relative to external anatomical landmarks, such as the trochanteric fossa, in an effort to position the osteotome to cut the desired bone leading to the femoral canal. Since every bone is shaped differently, the surgeon may not correctly predict the starting position which would lead to the desired bone removal. This may be further exacerbated by a poor grip between the osteotome and the bone surface, resulting in slippage of the osteotome after initial placement caused by impaction strikes.

The surgeon also conventionally angles the osteotome relative to the external anatomical landmarks, such as the femoral leg axis, in an effort to direct the angle that the osteotome resects the bone. Since it is often difficult to visualize the external anatomical landmarks and to hold the osteotome at the desired angle while impacting, the surgeon may not achieve the desired angle of bone removal.

The necessary amount of lateral bone may not be fully removed by the first cut. This is particularly true if the surgeon adopts a conservative and iterative bone cutting approach. Thus, further cuts with the osteotome, or removal of the bone with other instruments (e.g., rasp, rotational initiator or broach) may be required.

There is therefore a need for an improved osteotome that does not rely on external visual landmarks for positioning. There is also a need for an osteotome having an improved grip on the proximal surface of the femur.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

The invention provides an osteotome which includes a curved guide member extending distally from its medial side. This curved guide member interfaces with the medial curvature of the femoral canal. The guide member guides the osteotome using the internal bone geometry of the femoral canal instead of relying on external anatomical landmarks.

During initial positioning, the guide member provides haptic feedback of the location of the femoral canal. During impaction, the guide member helps to position and align the osteotome with the curvature of the femoral canal.

According to an aspect of the invention, there is provided an osteotome for preparing a proximal end of a femur of a patient for installation of a stem of a femoral component of a prosthetic hip during hip replacement surgery, the osteotome comprising:

a body having:
a proximal end connectable to a handle and
a distal end having a cutting edge; and
a curved guide member extending in a distal direction from the distal end of the body.

In some constructions, the curved guide member extends distally from the medial side of the osteotome.

In some constructions, the curved guide member comprises;
a shaft with a longitudinal length, the shaft having;
a proximal end,
a distal tip,
a lateral face, and
a medial face,
in which each of the lateral face and medial face has a longitudinal curve extending between the proximal end of the guide member and the distal tip. The distal tip may be substantially straight. A distal tip that mimics the distal shape of a number of the broaches used to prepare the femoral canal and/or the femoral stem implant component may be provided.

Advantageously, the curved guide member has a profiled outer surface for removing bone. This provides the osteotome with broach functionality. The profiled outer profile may comprise a plurality of cutting elements. The cutting elements may be disposed along the length of at least one of the lateral face and the medial face of the curved guide member. The cutting elements may be in the form of cutting teeth.

The osteotome's cutting edge may include a least one tooth extending distally therefrom. For example, a "shark" tooth. Upon impaction of the osteotome, the at least one tooth bites into the proximal surface of the femur. This helps to maintain the rotational position of the osteotome on the bone surface and prevents slipping. As a result, the initial placement of the osteotome on the proximal surface of the femur is maintained, even during impaction strikes.

In some constructions, the distal tip of the curved guide member includes a plurality of longitudinal flutes disposed along its exterior surface. These flutes are adapted to remove bone when the curved guide member is inserted into the intramedullary canal. In some constructions, the flutes are provided with a blunt edge which enables the user to easily rotate the device in order to create a hole in the cancellous bone.

In some constructions, a lateral side of the body of the osteotome is provided with a plurality of cutting teeth. This provides the osteotome with rasp functionality. The plurality of lateral cutting teeth are adapted such that any bone which is located laterally of the piriforma fossa, such as the greater trochanter, can be removed. Advantageously this rasping action provides the osteotome with the ability to be lateralised relative to the femoral canal. This results in the medial face of the curved guide member of the osteotome being located within the femoral canal such that it follows the medial curvature of the femoral bone.

The surgeon may find an osteotome provided with a depth indicator useful. The depth indicator may indicate to the surgeon the depth that the curved guide member of the osteotome should be progressed into the femoral canal in order to create the required depth of cavity. This depth indicator may take the form of an indicium provided on a wall of the body of the osteotome. This indicium may be a line. This line may be formed by the interface of two regions of the body of the osteotome. The interface may be a visual interface formed between two regions each having a different colour or textured surface.

The osteotome of the present invention may be a box osteotome. During hip arthroplasty, the box osteotome cuts a box shape out of the femoral bone to open the patient's femoral canal.

The box osteotome is generally provided with at least one window through which the surgeon can remove the resected bone during use. This window also enables cleaning of the device. Ideally, the at least one window is provided on a wall of the body of the box osteotome which allows the surgeon to hold the device without encountering any of the cutting teeth and also facilitates ease of cleaning.

The osteotome can be achieved by manufacturing using conventional manufacturing processes known in the art. The osteotome may formed by three-dimensional printing. The osteotome may be formed by a moulding technique, such as metal injection moulding (MIM).

According to still further aspect of the invention, there is provided a kit comprising an osteotome as herein described and a broach having a medial face and a lateral face, in which the curve of at least the medial face of the osteotome matches a curve of the medial face of the broach. This ensures that the medial face of the curved guide member of the osteotome interfaces with the medial curvature of the femoral canal in the same manner as that of the medial face of the broach.

Advantageously, the outer profile of the curved guide member matches the outer profile of the smallest broach. This provides the curved guide member with the functionality of a starter broach. This prepares the bone cavity for further broaching. The fact that the outer profile of the curved guide member matches the outer profile of the smallest broach also ensures that one size of osteotome is safe to be used for all stem sizes.

According to further aspect of the invention, there is provided a kit comprising an osteotome as herein described and a femoral stem component having a medial face and a lateral face, in which the curve of at least the medial face of the osteotome matches a curve of the medial face of the femoral stem component. This ensures that the medial face of the curved guide member of the osteotome interfaces with the medial curvature of the femoral canal in the same manner as that of the medial face of the femoral stem component.

According to further aspect of the invention, there is provided a method of preparing a proximal end of a femur for installation of a femoral component of a prosthetic hip, comprising steps of:
 (a) using an osteotome comprising:
  a body having
   a proximal end connectable to a handle and
   a distal end having a cutting edge; and
  a curved guide member extending in a distal direction from the distal end;
 (b) positioning the osteotome at a proximal end of the femur;
 (c) inserting a distal end of the curved guide member into a canal of the femur;
 (d) shaping the proximal end of the femur with the osteotome.

BRIEF DESCRIPTION OF THE DRAWINGS

Constructions of the guided osteotome will be described hereinafter, by way of example only, with reference to the accompanying drawings in which like reference signs relate to like elements and in which.

DETAILED DESCRIPTION

Constructions of the guided osteotome are described in the following with reference to the accompanying drawings.

Figure 1:
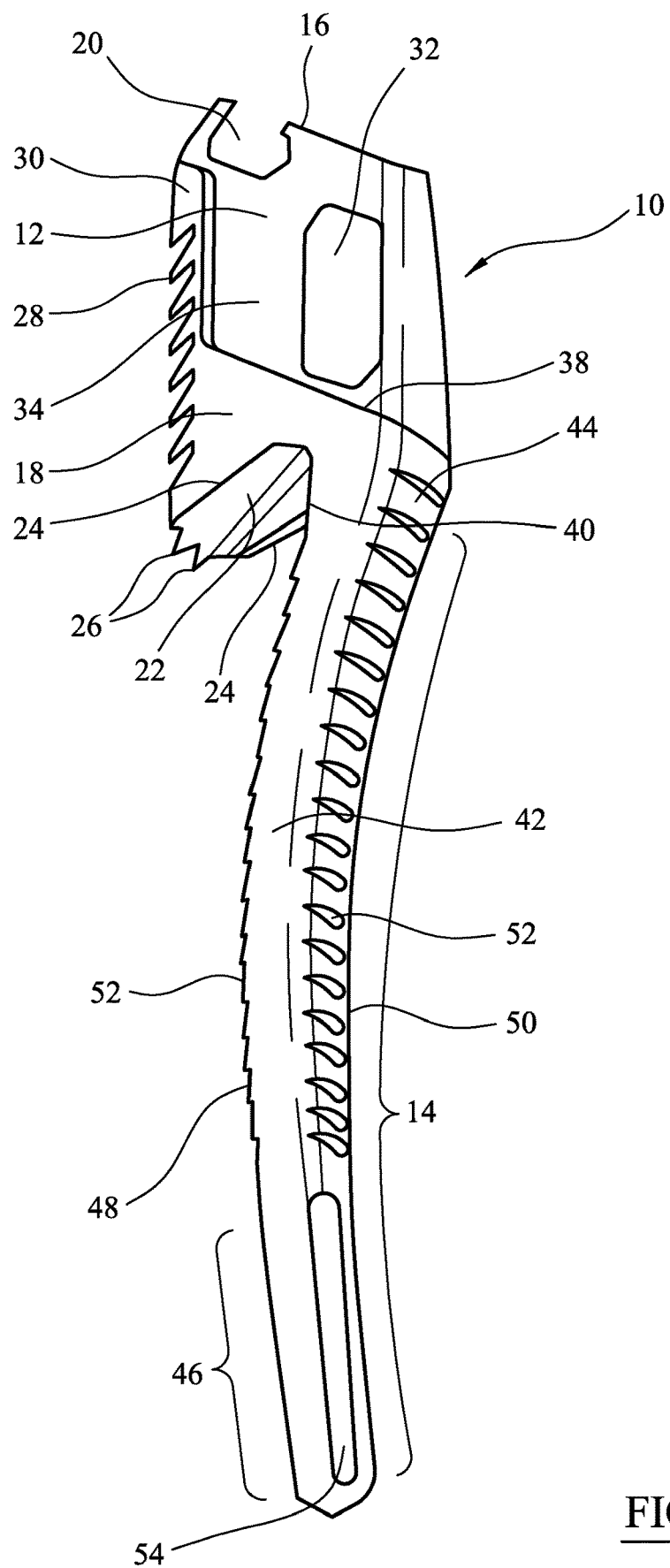
FIG. 1 is a schematic of a medial/lateral view of a first construction of an osteotome.

Referring now to FIG. 1, there is shown a box osteotome 10 for use in preparing the proximal end of a patient's femur. The osteotome includes a body 12 and a curved guide member 14.

The body 12 has a proximal end 16 and a distal end 18. The proximal end 16 includes a connection element 20 that is adapted to facilitate the releasable connection of the osteotome to a handle, such as a broach handle. As shown, the connection element 20 is a female connection element that is adapted to connect with a male connection element on a handle. In other constructions, the connection element is a male connection element that is adapted to connect with a female connection element on a handle.

The distal end 18 includes a generally rectangular aperture 22 that extends proximally into the body of the osteotome. The outer periphery of the aperture is bordered by a cutting edge 24. A plurality of cutting elements 26, shown here in the form of shark teeth, extend distally from the lateral edge 28 of the aperture 22. The shark teeth help to anchor the osteotome within the proximal surface of the femur and prevent slippage during impaction. A plurality of cutting elements 28 are also provided on the lateral face 30 of the body. Cutting elements 28 provide the osteotome with a rasping functionality. This facilitates removal of laterally located bone, such as the areas of the greater trochanter.

Figure 2:
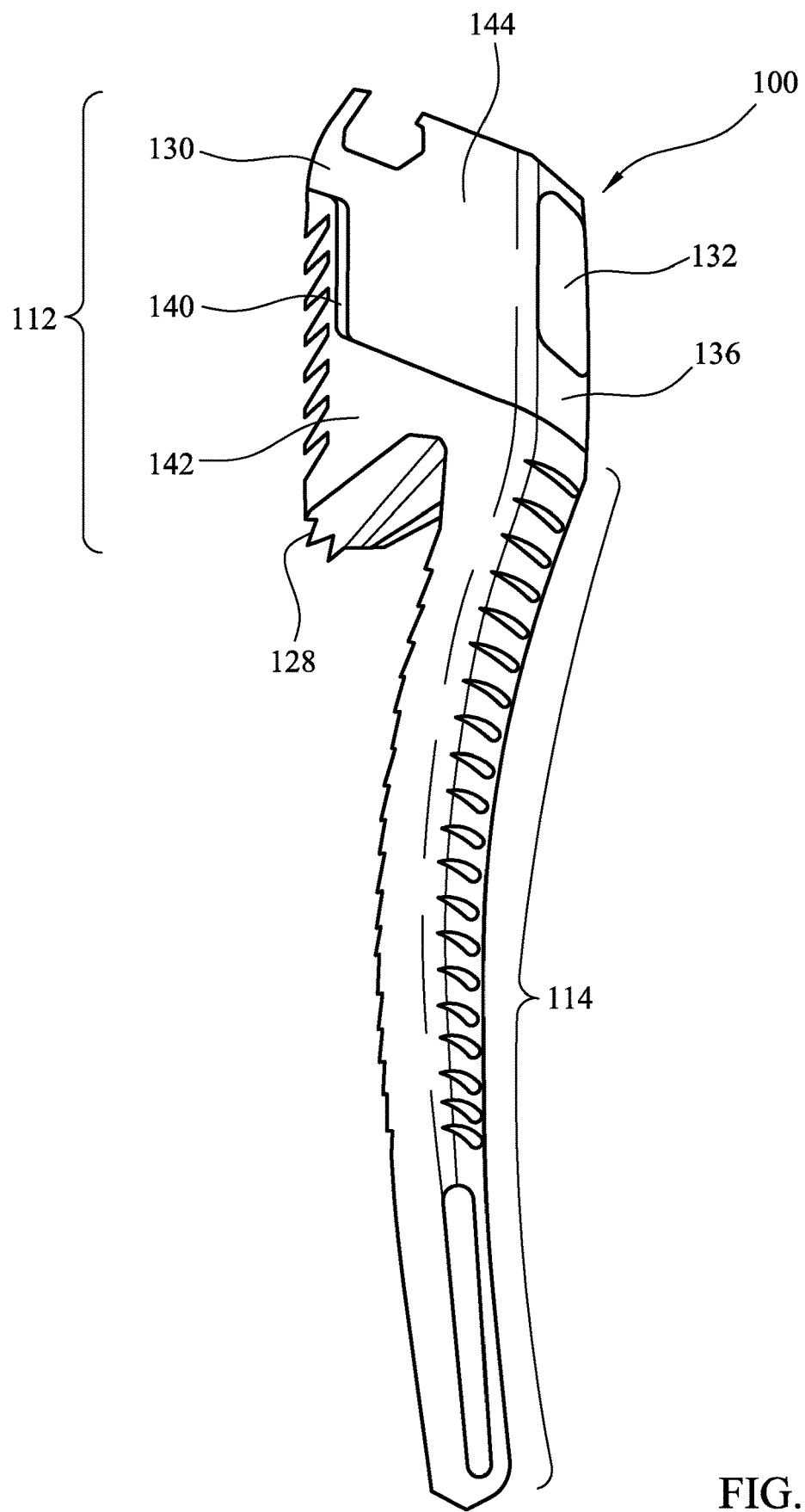
FIG. 2 is a schematic of a medial/lateral view of a second construction of the osteotome.

The body also includes a window 32 through which resected bone is removed. The window also aids with the cleaning of the osteotome. The window is connected to the aperture 22. The window 32 in the construction shown is provided on the anterior face 34 of the body 12. However, the window can be provided on other external faces of the body. Preferably, the window is provided on the body in a location that enables the surgeon to handle the device away from any of the cutting elements. For example, as shown in FIG. 2, in a second construction of the box osteotome, the window 132 is provided on the medial side 136 of the body.

This enables the surgeon to grip the device about the anterior face and the posterior face (not shown).

Figure 3:
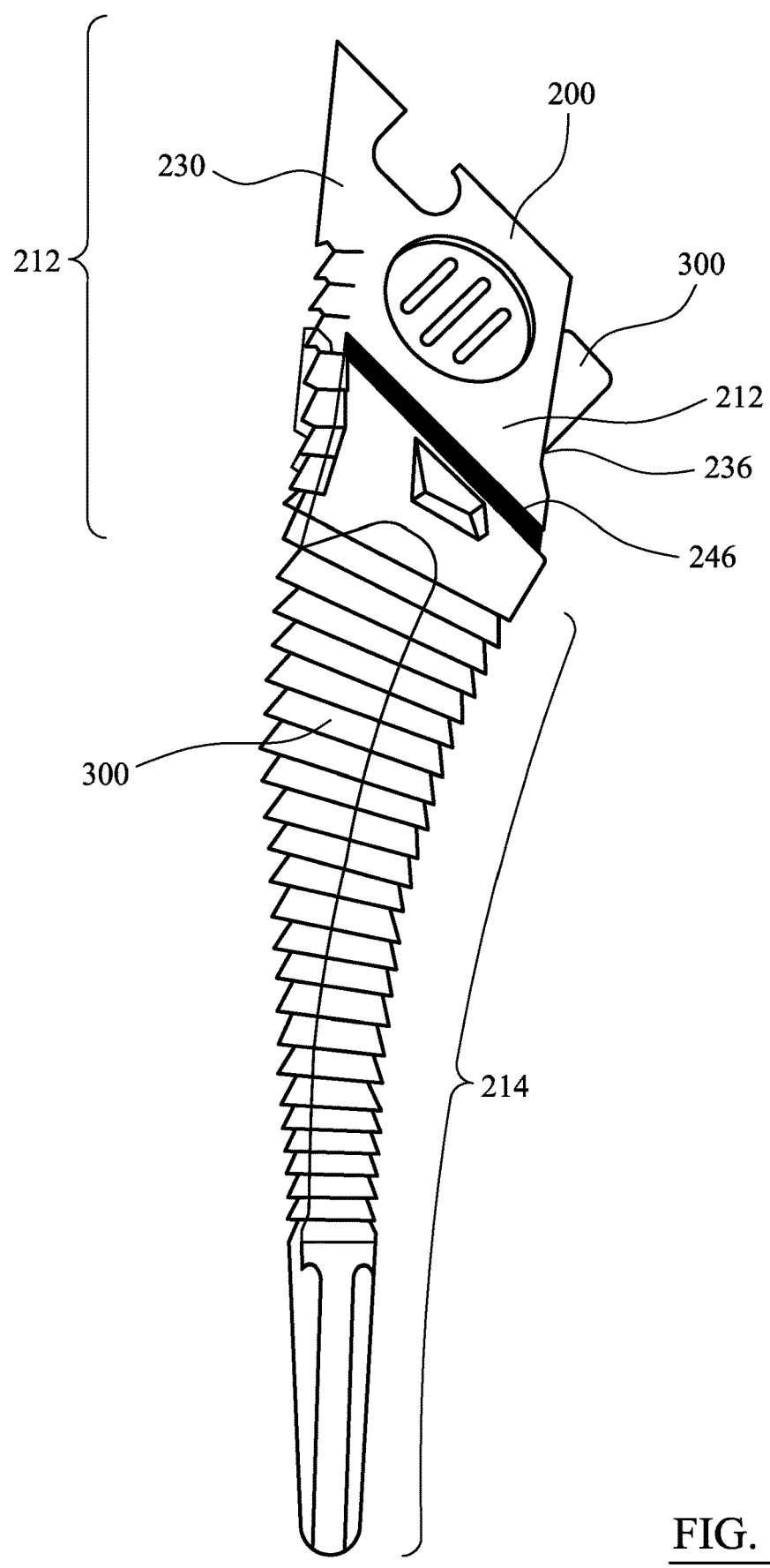
FIG. 3 is a superimposed image of a third construction of the osteotome and a starter broach.
Figure 4:
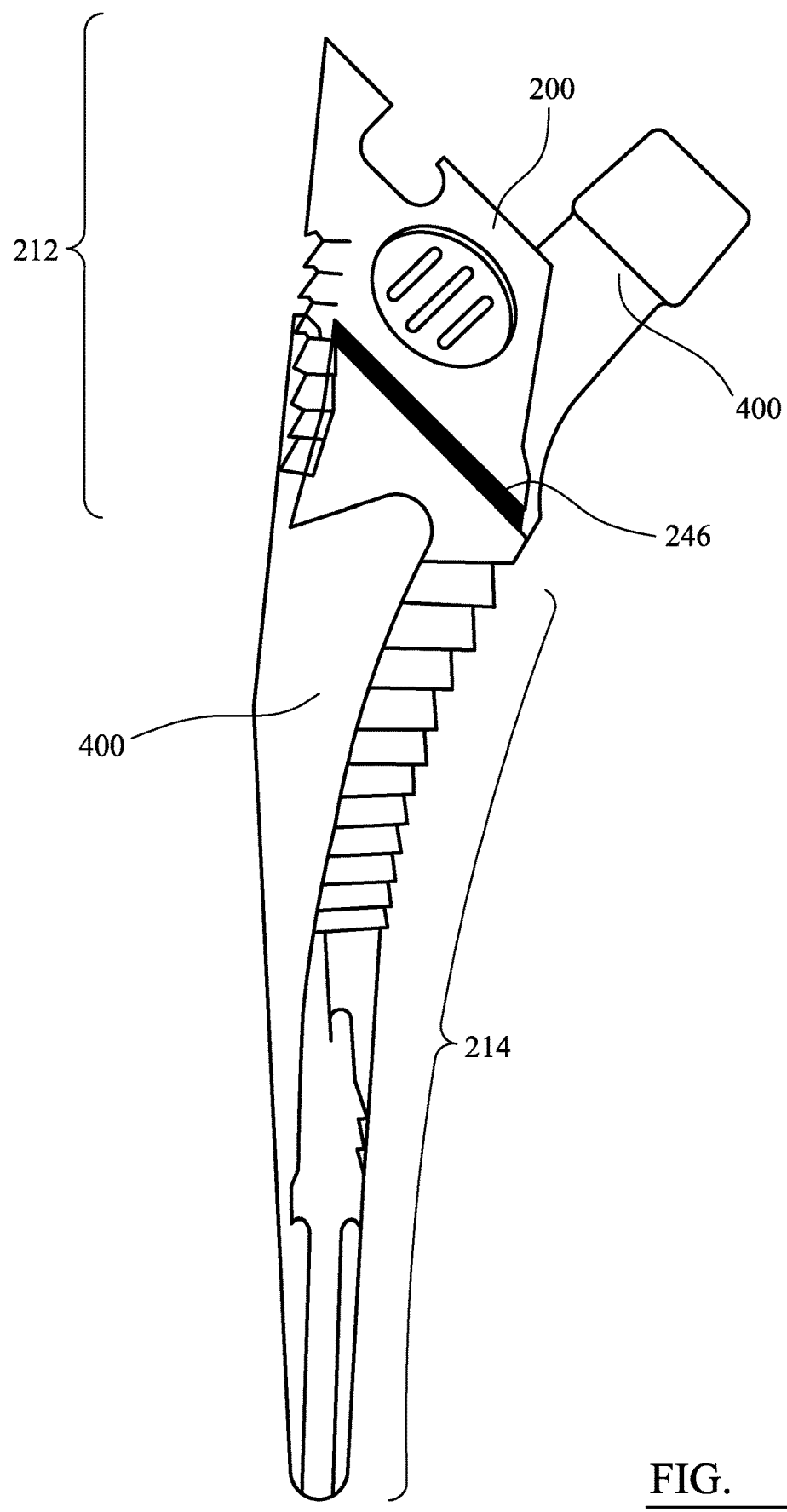
FIG. 4 is a superimposed image of a third construction of the osteotome and a femoral stem component.

The body 12 may also be provided with a depth indicator. The depth indicator can be used to indicate to the surgeon the depth that the curved guide member 14 should be progressed into the femoral canal in order to create a cavity having a depth that generally matches the longitudinal length of a starter broach or femoral stem component. In the first construction (FIG. 1), the depth indicator takes the form of a raised edge 38 extending at least partially between the lateral face 30 and medial 36 face of the body. In the second construction (FIG. 2), the depth indicator is formed by the interface 140 between a first region 142 of the body 12 having a first colour (e.g., silver) and a second region 144 of the body 12 having a second colour (e.g. black). The interface 140 extends at least partially between the lateral face 130 and medial 136 face of the body 112. In the third construction (FIGS. 3 and 4), the depth indicator takes the form of a line 246 applied, for example by laser marking, to the body of the device. The line extends at least partially between the lateral face 230 and medial face 236 of the body 212.

Referring again to FIG. 1, the curved guide member 14 extends from the medial edge 40 of the aperture 22. The curved guide member includes a longitudinal shaft 42 with a proximal end 44, a distal tip 46, a lateral face 48 and a medial face 50. The lateral face 48 and the medial face 50 have a longitudinal curve extending between the proximal end 44 of the curved guide member and the distal tip 46. Advantageously, the curvature of the medial face 50 is designed to generally match the curvature of the medial face of the starter broach 300 to be used in the preparation of the femur, and also the femoral stem component 400 to be implanted within the femur. This is shown with reference to a third construction of the osteotome, in FIG. 3 (an overlapping image with a starter broach) and FIG. 4 (an overlapping image with a femoral stem component).

In the construction shown, cutting elements 52 are disposed along both the lateral face 48 and the medial face 50 of the curved guide member. In other constructions, the cutting elements may be disposed on only one of the lateral face 48 or the medial face 50. The cutting elements 52 provide the osteotome with a broaching functionality.

The distal tip 46 of the curved guide member 14 includes a plurality of longitudinally extending flutes 54. These flutes 54 are adapted to remove bone when the curved guide member is inserted into the intramedullary canal. The flutes 54 may have a blunt edge. This enables the user to easily rotate the osteotome in order to create a hole in the cancellous bone. The distal tip of the curved guide member may be designed to generally match geometry of the distal tip of the broaches used to prepare the intramedullary canal and/or the femoral stem component.

In use, the surgeon or other operator would use the osteotome 10 which would include the body 12 having the proximal end 16 connectable to the handle (not shown) and the distal end 18 having the cutting edge 24. The osteotome 10 would also include the curved guide member 14 extending in a distal direction from the distal end 18. The user would then position the osteotome 10 at a proximal end of the femur and insert the distal end of the curved guide member into a canal of the femur. Using the osteotome, the operator would shape the proximal end of the femur with the osteotome.

Although particular constructions of the invention have been described, it will be appreciated that many modifications/additions and/or substitutions may be made within the scope of the claimed invention.

The invention claimed is:

1. An osteotome for preparing a proximal end of a femur of a patient for installation of a stem of a femoral component of a prosthetic hip during hip replacement surgery, the osteotome comprising:
    a body having
    a proximal end connectable to a handle, and
    a distal end having a cutting edge, wherein the distal end includes an aperture extending proximally into the body of the osteotome, and the aperture being bordered by the cutting edge, and
    a curved guide member extending in a distal direction from the distal end of the body in which the curved guide member further includes cutting elements.

2. The osteotome of claim 1, in which the distal end of the body has a medial side from which the curved guide member extends.

3. The osteotome of claim 1, in which the curved guide member comprises;
    a shaft with a longitudinal length, the shaft having;
    a proximal end,
    a distal tip,
    a lateral face, and
    a medial face,
    in which each of the lateral face and medial face has a longitudinal curve extending between the proximal end of the guide member and the distal tip.

4. The osteotome of claim 1, in which the cutting elements are disposed along the length of at least one of the lateral face and the medial face.

5. The osteotome of claim 1, in which the cutting edge comprises at least one tooth extending distally therefrom.

6. The osteotome of claim 3, in which the distal tip comprises a series of longitudinally disposed flutes.

7. The osteotome of claim 1, in which the osteotome is a box osteotome.

8. An osteotome for preparing a proximal end of a femur of a patient for installation of a stem of a femoral component of a prosthetic hip during hip replacement surgery, the osteotome comprising:
    a body having
    a proximal end connectable to a handle, and
    a distal end having a cutting edge, wherein the distal end includes an aperture extending proximally into the body of the osteotome, and the aperture being bordered by the cutting edge in which the cutting edge comprises at least one tooth extending distally therefrom, and
    a curved guide member extending in a distal direction from the distal end of the body.

9. The osteotome of claim 8, in which the distal end of the body has a medial side from which the curved guide member extends.

10. The osteotome of claim 8, in which the curved guide member comprises:
    a shaft with a longitudinal length, the shaft having;
    a proximal end,
    a distal tip,
    a lateral face, and
    a medial face,
    in which each of the lateral face and medial face has a longitudinal curve extending between the proximal end of the guide member and the distal tip.

11. The osteotome of claim 8, in which the curved guide member further includes cutting elements.

12. The osteotome of claim 10, in which the cutting elements are disposed along the length of at least one of the lateral face and the medial face.

13. The osteotome of claim 11, in which the distal tip comprises a series of longitudinally disposed flutes.

14. The osteotome of claim 8, in which the osteotome is a box osteotome.

\* \* \* \* \*